US011376207B2

(12) United States Patent
Lee et al.

(10) Patent No.: US 11,376,207 B2
(45) Date of Patent: *Jul. 5, 2022

(54) HAIR CARE COMPOSITIONS

(71) Applicant: L'OREAL, Paris (FR)

(72) Inventors: Heather Yoonsoo Lee, Wayne, NJ (US); Angela Park, Jersey City, NJ (US)

(73) Assignee: L'OREAL, Paris (FR)

( * ) Notice: Subject to any disclaimer, the term of this patent is extended or adjusted under 35 U.S.C. 154(b) by 16 days.

This patent is subject to a terminal disclaimer.

(21) Appl. No.: 15/799,229

(22) Filed: Oct. 31, 2017

(65) Prior Publication Data

US 2019/0125650 A1    May 2, 2019

(51) Int. Cl.
A61K 8/73     (2006.01)
A61Q 5/02     (2006.01)
A61K 8/04     (2006.01)
A61K 8/365    (2006.01)
A61K 8/44     (2006.01)
A61K 8/37     (2006.01)

(52) U.S. Cl.
CPC ............... A61K 8/73 (2013.01); A61K 8/046 (2013.01); A61K 8/365 (2013.01); A61K 8/375 (2013.01); A61K 8/44 (2013.01); A61K 8/731 (2013.01); A61K 8/737 (2013.01); A61Q 5/02 (2013.01)

(58) Field of Classification Search
CPC . A61K 8/73; A61K 8/44; A61K 8/365; A61K 8/046; A61K 8/737; A61K 8/375; A61K 8/731; A61Q 5/02
See application file for complete search history.

(56) References Cited

U.S. PATENT DOCUMENTS

| | | | |
|---|---|---|---|
| 4,292,426 A | 9/1981 | Orii et al. | |
| 8,193,137 B2 | 6/2012 | Kunieda et al. | |
| 8,518,991 B2 | 8/2013 | Gunn et al. | |
| 10,265,261 B2 | 4/2019 | Park et al. | |
| 2003/0059382 A1 | 3/2003 | Brandt et al. | |
| 2004/0156805 A1 | 8/2004 | Kazmi et al. | |
| 2009/0181060 A1 | 7/2009 | Rosato et al. | |
| 2009/0185989 A1 | 7/2009 | Golz-Bemer et al. | |
| 2009/0270297 A1 | 10/2009 | Luciow et al. | |
| 2009/0305929 A1 | 12/2009 | Luciow et al. | |
| 2010/0280111 A1 | 11/2010 | Aoki et al. | |
| 2011/0223125 A1* | 9/2011 | Hough | A61K 8/86 424/70.12 |
| 2011/0256085 A1* | 10/2011 | Talingting Pabalan | C08L 5/00 424/70.13 |
| 2014/0186284 A1* | 7/2014 | Sha | A61K 8/8176 424/70.13 |
| 2014/0349902 A1* | 11/2014 | Allef | A61K 8/361 510/119 |
| 2015/0297489 A1 | 10/2015 | Kleinen et al. | |
| 2016/0120803 A1 | 5/2016 | Mathur et al. | |
| 2016/0296448 A1 | 10/2016 | Terrisse et al. | |
| 2017/0000713 A1 | 1/2017 | Bakes et al. | |
| 2017/0071835 A1* | 3/2017 | Schelges | A61K 8/41 |
| 2017/0079898 A1 | 3/2017 | Fevola et al. | |
| 2017/0239155 A1 | 8/2017 | Hartnett et al. | |
| 2017/0333332 A1 | 11/2017 | Jia et al. | |
| 2018/0116937 A1 | 5/2018 | Park et al. | |
| 2018/0168945 A1 | 6/2018 | Schoepgens et al. | |
| 2019/0262246 A1* | 8/2019 | Liang | A61Q 5/02 |
| 2020/0170894 A1* | 6/2020 | Park | A61K 8/42 |
| 2020/0276099 A1 | 9/2020 | Robbins et al. | |

FOREIGN PATENT DOCUMENTS

| | | |
|---|---|---|
| DE | 10044662 A1 | 3/2002 |
| DE | 10 2006 008920 B3 | 8/2007 |
| DE | 20 2015 005 287 U1 | 10/2015 |
| EP | 1716842 A1 | 11/2006 |
| EP | 2335681 A1 | 6/2011 |
| EP | 2505180 A1 | 10/2012 |
| EP | 2532343 A1 | 12/2012 |
| EP | 3006088 A1 | 4/2016 |
| FR | 3018044 A1 | 9/2015 |
| WO | 2016079007 | 5/2016 |
| WO | 2016079008 | 5/2016 |
| WO | 2016079009 | 5/2016 |
| WO | 2017/099559 A1 | 6/2017 |
| WO | 2017/106276 A1 | 6/2017 |
| WO | 2018/002557 A1 | 1/2018 |
| WO | 2019/000394 A1 | 1/2019 |

OTHER PUBLICATIONS

Mintel, mintel.com, Sep. 13, 2016. pp. 1-6.
International Search Report and Written Opinion for counterpart Application No. PCT/US2019/019748, dated Apr. 23, 2019.
Non-Final Office Action for copending U.S. Appl. No. 15/907,784, dated Mar. 27, 2020.
Non-Final Office Action for copending U.S. Appl. No. 16/204,591, dated Sep. 23, 2020.
"Jason Shampoo and Conditioner" web product page (Oct. 9, 2016), Obtained from <https://www.burpy.com/whole-foods/jason-dandruff-relief-2-in-1-shampoo-conditioner-treatment/product-detail/1367207.
Mintel: "Gentle Conditioning Shampoo," Caudalie, Record ID 3537355, published Nov. 2015, pp. 1-2.
Mintel: "Anti-Dandruff Shampoo," Melvita, Record ID 298774, published Sep. 2004, pp. 1-2.
Mintel: "Exfoliating Scalp Shampoo," Kanellia, Record ID 3384671, published Oct. 15, pp. 1-2.

(Continued)

Primary Examiner — Robert A Wax
Assistant Examiner — Quanglong N Truong
(74) Attorney, Agent, or Firm — The Marbury Law Group, PLLC

(57) ABSTRACT

The present disclosure relates to composition and method for treating hair. A hair care composition comprising, in a cosmetically acceptable solvent: (a) one or more carboxylate anionic surfactants; (b) one or more cationic guar compounds; (c) one or more polysaccharide gums; and (d) one or more glyceryl esters, present in a total amount of at least 2 wt. % based on the total weight of the hair are composition. The composition of the present invention may optionally comprise one or more secondary surfactants.

19 Claims, No Drawings

(56) References Cited

OTHER PUBLICATIONS

Mintel: "Charcoal + Coconut Oil Micro-Exfoliating Shampoo," Briogeo Scalp Revival, Record ID 4787991, published Jun. 2017, pp. 1-5.
International Search Report and Written Opinion for counterpart Application No. PCT/US2020/019408, dated May 14, 2020.
Mintel: "Pureness Shampoo," Biopoint, XP055692070, Aug. 8, 2018.
Non-Final Office Action for copending U.S. Appl. No. 16/796,865, dated Dec. 8, 2020.
Song et al., "Homogeneous Quaternization of Cellulose in NaOH/Urea Aqueous Solutions as Gene Carriers," Biomacromolecules, 2008, 9, pp. 2259-2264.
LAMESOFT® PO 65 Data Profile, carechemicals, 2007, Revision Jul. 14, 2007.
Final Office Action for copending U.S. Appl. No. 16/204,591, dated May 3, 2021.
Final Office Action for copending U.S. Appl. No. 16/796,865, dated May 21, 2021.
International Preliminary Report on Patentability for counterpart Application No. PCT/US2019/061990, dated Jun. 10, 2021.
Mintel: "Straight Away Shampoo," GAG Beauty, XP002784087, Database Record No. 2451989, Jun. 1, 2014.
Mintel: "2in1 Treatment Shampoo + Conditioner," Hain Celestial Group, XP055652236, Database accession No. 5909775, Aug. 22, 2018.
Mintel: "All Access Go Anywhere Shampoo Bar," TIGI Rockaholic, XP055522683, Database accession No. 2099043, Jun. 20, 2013.
Mintel: "Gentle Conditioning Shampoo," Caudalie, XP055593329, Database accession No. 1417812, Oct. 19, 2010.
Final Office Action for copending U.S. Appl. No. 16/204,591, dated May 18, 2022.
English translation of JP2006028095 (2022).

* cited by examiner

HAIR CARE COMPOSITIONS

FIELD OF THE DISCLOSURE

The present invention relates to hair care compositions comprising one or more carboxylate anionic surfactants, one or more cationic guar compounds, one or more polysaccharide gums, and one or more glyceryl esters, in a cosmetically acceptable solvent. The disclosure also relates to methods of applying the hair care composition to hair in order to improve the manageability of hair.

BACKGROUND

Individuals desire healthy and strong hair, as healthy looking hair is in general a sign of good health and good hair-care practices. Nonetheless, nutrition, environmental influences, and chemical hair treatments can lead to hair damage that significantly weakens and dulls the hair over time. Gloss and moisture balance are deleteriously affected making the hair more difficult to manage and style. Furthermore, dry hair that has been weakened or damaged is also prone to breakage and the formation of "split ends."

The environment also influences the health of hair. Regions with hard water can affect the look, feel and shine of the hair. This is because hard water leaves mineral deposits, which accumulate over time on the hair and eventually prevents moisture intake into the hair. The hair becomes dry, frizzy, and is prone to tangles. Environmental factors, such as strong sun, wind, cold air, extreme temperature variations and changes in air humidity can also damage the hair. The static and dry winter air contributes to moisture loss.

Hair has a tendency to lose some of its qualities due to action of factors especially such as natural regressing, sweat, the removal of squamae, pollution or humidity. The visual appearance and the feel of the hair can thus be damaged. Regressing, for example, makes the hair lank, which then has a tendency to clump together. The hair may be increasingly difficult to style, and may have an unpleasant greasy sheen or an unpleasant waxy feel.

It is known practice to cleanse the hair with shampoos, which are generally aqueous compositions containing large amounts of sulfate-based surfactants, which are generally anionic surfactants, alone or in combination with amphoteric and/or nonionic surfactants. In order to provide good foaming qualities to the shampoos, the total amounts of sulfate-based anionic surfactants used usually exceed 10% by weight of active material relative to the total weight of the shampoos.

These shampoos based on large amounts of sulftate-based anionic surfactants may cause discomfort such as stinging of the scalp or of the eyes when they come into contact with the shampoo.

In addition, the rinsing of cosmetic compositions with a high content of surfactants may often be long.

Moreover, gradually in the course of their applications, these surfactants may impair the cosmetic properties of the hair, thus leading to the need also to use conditioning agents such as cationic polymers, silicones or non-silicone oils.

Finally, to avoid running on application and especially running into the eyes, shampoos should generally be thickened; but their thickening may pose problems of stability of the composition.

Thus, manufactures continuously seek to formulate shampoos and other hair care products using ingredients and combination of ingredients that can minimize or prevent the above-described disadvantages.

However, although the new formulation and products can afford detergency similar to that obtained with a standard shampoo, the products thus obtained can still have insufficient foaming nature; in addition, the cosmetic properties imparted to the hair can still not be entirely satisfactory, in particular on dry hair.

SUMMARY OF THE DISCLOSURE

The aim of the present invention is to propose cosmetic hair compositions that overcome these drawbacks, and especially that are capable of generating an adequate foam, both in quality and quantity, and that give the hair satisfactory cosmetic properties, most particularly on dry hair.

The present invention relates to a cosmetic composition, especially a hair composition.

One aspect of the present invention pertains to a hair care composition comprising, in a cosmetically acceptable solvent: (a) one or more carboxylate anioinic surfactant; (b) one or more catioinic guar compounds; (c) one or more polysaccharide gums; (d) one or more esters, present in a total amount of at least 2 wt. % based on the total weight of the hair care composition.

Another aspect of the present invention pertains to a method of cleansing hair, the method comprising applying the hair care composition comprising, in a cosmetically acceptable solvent: (a) one or more carboxylate anioinic surfactants; (b) one or more catioinic guar compounds; (c) one or more polysaccharide gums; (d) one or more glyceryl esters, present in a total amount of at least 2 wt. % based on the total weight of the hair care composition onto hair.

In one or more embodiments, the method provides improved manageability to hair.

DETAILED DESCRIPTION OF THE DISCLOSURE

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. The compositions of the disclosure may be free of the component(s) or may be "substantially free" or "essentially free" of the component(s) described for optional inclusion in said compositions. Nonetheless, the compositions may include less than about 1 wt.

%, less than about 0.5 wt. %, less than about 0.1 wt. %, or none of the specified material or components The term "synthetic polymer" (or "synthetic film-forming polymer") means a polymer, which is purely synthetic, or not of natural origin, especially those polymers, which are made by radical polymerization of ethylenically unsaturated monomers or by polycondensation. The term "natural polymer" means a polymer of natural origin, which can be understood as a polymer of natural origin, which also can be subsequently chemically or physically modified.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

One aspect of the present invention pertains to a hair care composition comprising, in a cosmetically acceptable solvent: (a) one or more carboxylate anioinic surfactant; (b) one or more catioinic guar compounds; (c) one or more polysaccharide gums; and (d) one or more glyceryl esters, present in a total amount of at least 2 wt. % based on the total weight of the hair care composition.

In one or more embodiments, the one or more carboxylate anionic surfactants are selected from of acylglycinates, acylsarcosinates, palm itoylsarcosinates, stearoylsarcosinates, lauroylsarcosinates, cocoyacyllactylates, acyllactylates, behenoyllactylates, lauroyllactylates, (iso)stearoyllactylates, acylglutamates, and a mixture thereof. In one or more embodiments, the one or more carboxylate anionic surfactants are selected from stearoylglutamates, lauroylglutamates, cocoylglutamates, sodium cocoylglutamates, disodium cocoylglutamates, lauryl ether carboxylates, their salts, and a mixture thereof.

In one or more embodiments, the one or more carboxylate anionic surfactants are selected from of acylglycinates, acylsarcosinates, palm itoylsarcosinates, stearoylsarcosinates, lauroylsarcosinates, cocoyacyllactylates, acyllactylates, behenoyllactylates, lauroyllactylates, (iso)stearoyllactylates, acylglutamates, and a mixture thereof. In one or more embodiments, the one or more carboxylate anionic surfactants are selected from stearoylglutamates, lauroylglutamates, cocoylglutamates, sodium cocoylglutamates, disodium cocoylglutamates, lauryl ether carboxylates, their salts, and a mixture thereof.

In one or more embodiments, the one or more anionic surfactants comprises disodium cocoyl glutamate and sodium cocoyl glutamate.

In one or more embodiments, the total amount of the one or more anionic surfactants is from about 2% to about 13 wt. %, based on the total weight of the hair care composition. In one or more embodiments, the total amount of the one or more anionic surfactants is from about 4% to about 12 wt. %, based on the total weight of the hair care composition.

In one or more embodiments, the one or more cationic guar compounds are selected from the group consisting of hydroxypropyl guar hydroxypropyltrimonium chloride, guar hydroxypropyltrimonium chloride, and a mixture thereof.

In one or more embodiments, the cationic guar compound is hydroxypropyl guar hydroxypropyltrimonium chloride In one or more embodiments, the total amount of the one or more cationic guar compound is from about 0.1% to about 2 wt. %, based on the total weight of the hair care composition. In one or more embodiments, the total amount of the one or more cationic guar compound is from about 0.2% to about 1.5 wt. %, based on the total weight of the hair care composition.

In one or more embodiments, the one or more polysaccharide gums are selected from sclerotium gum, cellulose gum, nonionic guar gum, anionic guar gum, xanthan gum, diutan gum, carrageenan, gellan gum, welan gum, pectin, galactoarabinan, alginate, pullulan, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate and a mixture thereof.

In one or more embodiments, the one or more polysaccharide gums are selected from sclerotium gum, xanthan gum, pullulan and a mixture thereof.

In one or more embodiments, the total amount of the one or more polysaccharide gums is from about 0.1% to about 5 wt. %, based on the total weight of the hair care composition.

In one or more embodiments, the total amount of the one or more polysaccharide gums is from about 0.2% to about 3 wt. %, based on the total weight of the hair care composition.

In one or more embodiments, the one or more glyceryl esters are selected from glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate and a mixture thereof.

In one or more embodiments, the one or more glyceryl esters are selected from glyceryl caprylate, glyceryl caprylate/caprate, and a mixture thereof.

In one or more embodiments, the one or more glyceryl esters includes glyceryl caprylate.

In one or more embodiments, the total amount of the one or more glyceryl esters is from about 2% to about 6 wt. %, based on the total weight of the hair care composition.

In one or more embodiments, the total amount of the one or more glyceryl esters is from about 2% to about 5 wt. %, based on the total weight of the hair care composition.

In one or more embodiments, the cosmetically acceptable solvent is selected from the water, organic solvents and a mixture thereof.

In one or more embodiments, the hair care composition further comprises one or more secondary surfactants comprises non-carboxylate anionic surfactants, sulfate anionic sulfates, sulfonate anionic surfactant, nonionic surfactants, amphoteric surfactants and a mixture thereof.

In one or more embodiments, the hair care composition comprises one or more secondary surfactants selected from decyl glucoside, lauryl glucoside, coco-glucoside, cocoyl methyl glucamide, disodium laureth sulfosuccinate, sodium lauryl sulfoacetate, and a mixture thereof.

In one or more embodiments, the total amount of the one or more secondary surfactants is from about 0.1% to about 10 wt. %, from about 1% to about 8 wt. %, based on the total weight of the hair care composition. In one or more embodiments, the composition is substantially free of sulfate-based anionic surfactants.

The composition according to the present invention may be substantially free of silicones.

The composition accordingly to the present invention may be substantially free of sulfate-based anionic surfactants.

It has now been surprisingly and unexpectedly discovered that the combination of the carboxylate anionic surfactants, the cationic guar compounds, the polysaccharide gums, and glyceryl esters resulted in a composition with good foaming and cleansing properties.

Carboxylate Anionic Surfactants

The composition according to the present invention comprises one or more carboxylate anionic surfactants.

For the purpose of the present invention the term "carboxylate anionic surfactant" means an anionic surfactant comprising one or more carboxylic or carboxylate functions (—COOH or —COO—). They may also optionally comprise one or more sulfonate functions (—SO3H or —SO3-); preferably, however, the carboxylate anionic surfactants according to the present invention do not comprise any sulfonate functions.

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The carboxylic anionic surfactants that may be used thus comprise at least one carboxylic or carboxylate function (—COOH or —COO—).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds.

The alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group.

These compounds possibly being polyoxyalkylenated, especially polyoxyethylenated, and then preferably comprising from 1 to 50 ethylene oxide units and better still from 2 to 10 ethylene oxide units.

Use may also be made of the polyglycoside-polycarboxylic acids such as alkyl glucoside citrates, alkyl polyglycoside tartrates and alkyl polyglycoside sulfosuccinates, and alkylsulfosuccinamates, the alkyl group of these compounds comprising from 14 to 30 carbon atoms and better still from 16 to 22 carbon atoms, C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name AKYPO.

The polyoxyalkylenated alkyl (amido) ether carboxylic acids that may be used are preferably chosen from those of formula (1):

(1)

in which:
R1 represents a linear or branched C6-C24 alkyl or alkenyl radical, an alkyl(C8-C9) phenyl radical, a radical R2CONH—CH2-CH2- with R2 denoting a linear or branched C9-C21 alkyl or alkenyl radical,
preferably, R1 is a C8-C20 and preferably C8-C18 alkyl radical, and aryl preferably denotes phenyl, n is an integer or decimal number (average value) ranging from 2 to 24 and preferably from 2 to 10,
A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:
R1 denotes a C12-C14 alkyl, cocoyl, oleyl, nonylphenyl or octylphenyl radical,
A denotes a hydrogen or sodium atom, and
n varies from 2 to 20 and preferably from 2 to 10.

Even more preferentially, use is made of compounds of formula (1) in which R denotes a C12 alkyl radical, A denotes a hydrogen or sodium atom and n ranges from 2 to 10.

Salts that may be mentioned in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the carboxylic anionic surfactants are chosen, alone or as a mixture, from:
acylglutamates, especially of C6-C24 or even C12-C20, such as stearoylglutamates, and in particular disodium stearoylglutamate;
acylsarcosinates, especially of C6-C24 or even C12-C20, such as palmitoylsarcosinates, and in particular sodium palmitoylsarcosinate;
acyllactylates, especially of C12-C28 or even C14-C24, such as behenoyllactylates, and in particular sodium behenoyllactylate;
C6-C24 and especially C12-C20 acylglycinates;
(C6-C24)alkyl ether carboxylates and especially (C12-C20)alkyl ether carboxylates;
polyoxyalkylenated (C6-C24)alkyl(amido) ether carboxylic acids, in particular those comprising from 2 to 50 ethylene oxide groups; in particular in the form of alkali metal or alkaline-earth metal, ammonium or amino alcohol salts.

In certain embodiments, the carboxylate anionic surfactant may be chosen advantageously from acylglycinates, acylsarcosinates, acyllactylates and acylglutamates, the acyl groups preferably comprising from 14 to 30 carbon atoms and better still from 16 to 22 carbon atoms; and also the corresponding salified forms. These compounds may be optionally oxyethylenated and then preferably comprise from 1 to 50 ethylene oxide units and better still from 1 to 10 ethylene oxide units.

Preferentially, the carboxylate anionic surfactants are chosen from (C14-C30)acylglutamates and in particular stearoylglutamates, lauroylglutamates and cocoylglutamates; (C14-C30)acylsarcosinates and in particular palmitoylsarcosinates, stearoylsarcosinates, lauroylsarcosinates and cocoylsarcosinates; (C14-C30)acyllactylates and in particular behenoyllactylates, lauroyllactylates and (iso)stearoyllactylates; alkyl ether carboxylates and in particular lauryl ether carboxylates; and mixtures thereof, in particular in the form of alkali metal, alkaline-earth metal, ammonium, amine or amino alcohol salts.

Mention may be made more particularly of disodium cocoylglutamate and sodium cocyl glutamate.

In an embodiment, the one or more carboxylate anionic surfactants of the present invention may be selected from disodium cocoyl glutamate, sodium cocoyl glutamate and mixtures thereof.

In an embodiment, the one or more carboxylate anionic surfactants of the present comprise disodium cocoyl glutamate and sodium cocoyl glutamate.

The combination of disodium cocoyl glutamate and sodium cocoyl glutamate may be commercially available under the tradename AMISOFT CS 22, sold by the company Ajinomoto.

The one or more carboxylate anionic surfactants of the present invention may be employed in an amount of from about 2% to about 13% by weight, such as from about 4% to about 12% by weight, and further such as from about 4% to about 10% by weight, based on the total weight of the hair care composition of the present invention, including increments and ranges therein there between.

The total amount of the carboxylate anionic surfactants in the present invention may be employed in an amount from about 2, 3, 4, 5, 6, 7, 8, 9, 10, 11, 12, to about 13 percent weight, including increments and ranges therein there between.

Cationic Guar Compounds

The compositions of the present disclosure comprise one or more cationic guar compounds. Suitable examples of the one or more cationic guar compounds are non-cellulose cationic polysaccharides, such as guar gums containing trialkylammonium cationic groups. Suitable cationic guar gum derivatives are those given the PCPC (Personal Care Products Council, formerly CTFA, designation) of guar hydroxypropyl trimonium chloride, available commercially for example as JAGUAR C13S, which has a low degree of substitution of the cationic groups and a high viscosity. The low degree of cationic substitution leads to a cationic charge density of 0.0008. Other suitable materials include that known as JAGUAR C15, having a moderate degree of substitution and a low viscosity, JAGUAR C17 (high degree of substitution, hence cationic charge density of 0.0016, high viscosity) and JAGUAR C16 which is a hydroxypropylated cationic guar derivative containing a low level of substituent groups as well as cationic quaternary ammonium groups. JAGUAR C16 has a cationic charge density of 0.0008. Guar hydroxypropyl trimonium chloride, may also be available commercially for example as N-HANCE CG13 from the company Ashland, Also suitable is hydroxypropyl guar hydroxypropyltrimonium chloride, commercially available as JAGUAR 162, which is a high transparency, medium viscosity guar having a low degree of substitution.

Such products are sold, for example, under the trade names JAGUAR C135, JAGUAR C1000, JAGUAR C17, JAGUAR 162, JAGUAR C145, and JAGUAR EXCEL by the company Solvay (Rhodia).

In an embodiment, the one or more cationic guar compounds of the present disclosure are selected from hydroxypropyl guar hydroxypropyltrimonium chloride, commercially available under the tradename of JAGUAR 162, and guar hydroxypropyltrimonium chloride, commercially available under the tradename of JAGUAR C13S, both sold by Solvay (Rhodia), and a mixture thereof.

In an embodiment, the one or more cationic guar compounds of the present disclosure include hydroxypropyl guar hydroxypropyltrimonium chloride. The one or more cationic guar compounds of the present invention may be employed in an amount of from about 0.1% to about 2% by weight, such as from about 0.2% to about 1.5% by weight, and further such as from about 0.3% to about 1.0% by weight, based on the total weight of the hair care composition of the present invention, including increments and ranges therein there between.

The total amount of the one or more cationic guar compounds in the present invention may be employed in an amount from about 0.1, 0.2, 0.3, 0.4, 0.5, 0.6, 0.7, 0.8, 0.9, and 1.0 to about 2.0 percent weight, including increments and ranges therein there between.

Polysaccharide Gums

The hair care composition includes one or more polysaccharide gums. The polysaccharide gums may also function as thickening agents in the composition of the present invention. Thickening agents may also be referred to herein as rheology modifiers, thickening compounds, thickeners, gelling agents, and the like.

In some cases, the one or more polysaccharide gums may be chosen from starches, vegetable gums, and pectin). Non-limiting examples of polysaccharide gums include sclerotium gum, xanthan gum, diutan gum, carrageenan, gellan gum, welan gum, pectin, galactoarabinan, alginate, cellulose gum, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, pullulan and a mixture thereof. In some instances, sclerotium gum, pullulan and xanthan gum may be particularly useful.

The one or more polysaccharide gums of the present invention may be employed in an amount of from about 0.1% to about 5% by weight, such as from about 0.2% to about 3% by weight, and further such as from about 0.3% to about 2% by weight, based on the total weight of the hair care composition of the present invention, including increments and ranges therein there between.

The total amount of polysaccharide gums in the present invention may be employed in an amount from about 0.1, 0.2, 0.3, 0.4, 0.5, 0.6, 0.7, 0.8, 0.9, 1.0, 1.5, 2.0, 2.5, 3.0, 3.5, 4.0, 4.5 to about 5.0 percent weight, including increments and ranges therein there between.

Glyceryl Esters

The hair care composition includes one or more glyceryl esters. The glyceryl esters may also function as thickening agents, emulsifier in the composition of the present invention. Thickening agents may also be referred to herein as rheology modifiers, thickening compounds, thickeners, gelling agents, and the like.

Non-limiting examples of glyceryl esters (or (poly)glyceryl esters) include glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate; polyglyceryl-4 isostearate, polyglyceryl-3 oleate, polyglyceryl-2 sesquioleate, triglyceryl diisostearate, diglyceryl monooleate, tetraglyceryl monooleate, and a mixture thereof.

Even more suitable to the invention are the esters selected from mono- and/or di-glyceryl caprylate, mono- and/or di-glyceryl caprate, mono- and/or di-glyceryl heptanoate, mono- and/or di-glyceryl caprylate, and mixtures thereof.

More specifically, it is monoglyceryl caprylate (also known as glycerol caprylate), and mixtures thereof.

Examples include the compounds marketed under the name APMUL MCM or AKOLINE MCM (glyceryl caprylate/caprate) by Abitec, DERMOSOFT GMCY (glycerol caprylate) by STRAETMANS, CAPMUL 708 G (GLYCERYL CAPRYLATE and GLYCERYL DICAPRYLATE) by Abitec, as well as CAPMUL 907P (propylene glycol heptanoate) by ABITEC, as well as CAPMUL 908P (propylene glycol caprylate) from ABITEC.

According to one embodiment, the (poly)glyceryl ester according to the invention is selected from the group of glyceryl caprylate, polyglyceryl-3 caprylate, polyglyceryl-3 caprate, polyglyceryl-4 caprate, glyceryl laurate, polyglyceryl-2 laurate, polyglyceryl-5 laurate, polyglyceryl-10 laurate, glyceryl myristate, glyceryl stearate, glyceryl undecylenate, glyceryl caprylate/caprate, and mixtures thereof.

In particular, the compounds according to the invention comprise glyceryl caprylate as a (poly)glycerol ester.

The one or more glyceryl esters of the present invention may be employed in an amount of from about 2% to about 6% by weight, such as from about 2% to about 5% by weight, based on the total weight of the hair care composition of the present invention, including increments and ranges therein there between.

The total amount of the glyceryl esters in the present invention may be employed in an amount from about 2.0, 2.1, 2.2, 2.3, 2.4, 2.5, 2.6, 2.7, 2.8, 2.9, 3.0, 3.5, 4.0, 4.5, 5.0, 5.5 to about 6.0 percent weight, including increments and ranges therein there between.

Cosmetically Acceptable Solvents

Cosmetically acceptable solvents chosen from organic solvents, water-soluble solvents, water. Non-limiting examples of cosmetically acceptable solvents include, for example, organic solvents, such as C1-4 alcohols, polyols, glycols, and a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of cosmetically acceptable solvents are chosen from polyols which include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof. Polyhydric alcohols are useful.

Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some cases, the cosmetically acceptable solvent may be selected from the group consisting of one or more glycols, C1-4 alcohols, polyols, and a mixture thereof. In some cases, the cosmetically acceptable solvent is selected from the group consisting of hexylene glycol, propylene glycol, caprylyl glycol, glycerin, ethanol, isopropyl alcohol, and a mixture thereof.

The total amount of the one or more cosmetically acceptable solvents may vary but is typically about 0.1 to about 25 wt. %, based on the total weight of the present composition. In some cases, the total amount of the one or more water-soluble solvents may be about 0.1 to about 20 wt. %, about 0.1 to about 15 wt. %, about 0.1 to about 10 wt. %, about 0.5 to about 20 wt. %, about 0.5 to about 15 wt. %, about 0.5 to about 10 wt. %, about 2 to about 20 wt. %, about 2 to about 15 wt. %, about 5 to about 20 wt. %, or about 5 to about 15 wt. %, based on the total weight of the present compositions.

The total amount of water in the present compositions may vary but is typically about 50 to about 95 wt. %, based on the total weight of the present compositions. In some cases, the total amount of water is about 60 to about 90 wt. %, about 50 to about 85 wt. %, or about 60 to about 85 wt. %, based on the total weight of the composition.

Cationic Conditioning Agents

The compositions of the present invention may include additional cationic compounds other than the one or more cationic guar compounds described above. These additional cationic compounds can function as cationic conditioning agents and may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Cationic polymers useful in the hair care compositions may include, homopolymers and copolymers derived from acrylic or methacrylic esters or amides, copolymers of cellulose or cellulose derivatives grafted with a water-soluble quaternary ammonium monomer, polymers of piperazinyl units and of divalent alkylene or hydroxyalkylene radicals, cyclopolymers of alkyldiallylamine and of dialkyldiallylammonium, quaternary diammonium polymers, polyquaternary ammonium polymers, quaternary polymers of vinylpyrrolidone and of vinylimidazole, vinylamide homopolymers or copolymers, cationic polyurethane derivatives and mixture thereof.

Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; and MERQUAT100 and 280, a dimethyl dialkyl ammonium chloride (polyquaternium 6) available from Nalco.

Emulsifiers

The compositions of the present invention may include additional emulsifiers other than the one or more glyceryl esters described above. Useful emulsifiers may include, for example, fatty acids, fatty alcohols, esters of polyols and of a fatty acid, polyol fatty esters and fatty ethers with a branched or unsaturated chain containing from 10 to 30 carbon atoms, esters of sugar and of a fatty acid, and a mixture thereof. The fatty chains in the emulsifiers may be, for example from about 8 to about 35 carbon atoms in length, and may be saturated or unsaturated, and may be optionally branched. In some cases, the fatty chains are about 10 to about 30 carbon atoms in length or about 12 to about 24 carbon atoms in length.

Other useful emulsifiers that are glycol esters such as glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, and mixtures thereof.

pH Adjusters

The composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The hair care composition comprises one or more pH adjusters is selected from the citric acid, sodium hydroxide.

In particular, the compound according to the present invention comprises citric acid.

The total amount of the one or more pH adjusters is from about 0.01% to about 0.75 wt. %, such as from about 0.1% to about 0.60 wt. %, based on the total weight of the present invention, including increments and ranges therein there between.

The total amount of the one or more pH adjusters in the present invention may be employed in an amount from about 0.10, 0.15, 0.20, 0.25, 0.30, 0.35, 0.40, 0.45, 0.50, 0.55, 0.60, 0.65, 0.70 to about 0.75 percent weight, based on the total weight of the present invention, including increments and ranges therein there between.

The pH adjusters may, in various embodiments, be present in the hair care composition in an amount effective with a pH of about 5 to 6, about 5.1 to 6, about 5.2 to 6, about 5.3 to 6, about 5.4 to 6, about 5.5 to 6, about 5.6 to 6, about 5.7 to 6, about 5.8 to 6, about 5.9 to 6, about 5.1 to 5.9, about 5.2 to 5.9, about 5.3 to 5.9, about 5.4 to 5.9, about 5.5 to 5.9, about 5.6 to 5.9, about 5.7 to 5.9, about 5.8 to 5.9, about 5.1 to 5.8, about 5.2 to 5.8, about 5.3 to 5.8, about 5.4 to 5.8, about 5.5 to 5.8, about 5.6 to 5.8, about 5.7 to 5.8, including increments and ranges therein there within.

In an embodiment, the compositions of present invention are in form of an emulsion or a lotion or an aqueous composition.

In other embodiments, the composition of the present invention has a viscosity of from about 1,684 to about 3,360 cp, such as from about 1,894 to about 3,151 cp, such as from about 2,103 to about 2,942 cp, such as from about 2,313 to about 2,732 cp, including all ranges and subranges therebetween, as measured by a Rhéomat RM180 at 25° C. or other equivalent standard rheology or viscosity measuring device.

In an embodiment, the composition of the present invention has a viscosity of from 2,313 to about 2,732 cp, including all ranges and subranges therebetween.

Additional Surfactants

The composition according the present invention also comprises one or more additional surfactants, preferably chosen from nonionic surfactants, anionic surfactants other than the above listed carboxylate anionic surfactants, and amphoteric surfactants.

The anionic surfactants other than the above listed carboxylate anionic surfactants may be chosen from sulfonate anionic surfactants and sulfate anionic surfactants.

It is understood in the present description that:
the sulfonate anionic surfactants comprise at least one sulfonate function ($—SO_3H$ or $—SO_3^-$) and may optionally also comprise one or more sulfate functions, and/or one or more carboxylate functions; and
the sulfate anionic surfactants comprise at least one sulfate function and may additionally comprise comprise carboxylate and/or sulfonate functions.

The sulfonate anionic surfactants that may be used comprise at least one sulfonate function ($—SO3H$ or $—SO3-$).

In certain embodiments, the anionic surfactants may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds.

The alkyl groups of these compounds comprising from 6 to 30 carbon atoms, especially from 12 to 28, better still from 14 to 24 or even from 16 to 22 carbon atoms; the aryl group preferably denoting a phenyl or benzyl group.

These compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
C6-C24 and especially C12-C20 alkylsulfosuccinates, especially laurylsulfosuccinates;
C6-C24 and especially C12-C20 alkyl ether sulfosuccinates;
(C6-C24)acylisethionates and preferably (C12-C18)acylisethionates,
In particular in the form of alkali metal or alkaline-earth metal, ammonium or amino alcohol salts.

The sulfate anionic surfactants that may be used comprise at least one sulfate function ($—OSO3H$ or $—OSO3-$).

They may be chosen from the following compounds: alkyl sulfates, alkyl ether sulfates, alkylamido ether sulfates, alkylaryl polyether sulfates, monoglyceride sulfates; and also the salts of these compounds;

The alkyl groups of these compounds comprising from 6 to 30 carbon atoms, especially from 12 to 28, better still from 14 to 24 or even from 16 to 22 carbon atoms; the aryl group preferably denoting a phenyl or benzyl group;

These compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:
alkyl sulfates, especially of C6-C24 or even C12-C20,
alkyl ether sulfates, especially of C6-C24 or even C12-C20, preferably comprising from 2 to 20 ethylene oxide units;
In particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
C6-C24 and especially C12-C20 alkyl sulfates;
C6-C24 and especially C12-C20 alkyl ether sulfates; preferably comprising from 2 to 20 ethylene oxide units;
C6-C24 and especially C12-C20 alkylsulfosuccinates, especially laurylsulfosuccinates;
C6-C24 and especially C12-C20 alkyl ether sulfosuccinates;
(C6-C24)acylisethionates and preferably (C12-C18)acylisethionates;
C6-C24 and especially C12-C20 acylsarcosinates; especially palmitoylsarcosinates;
(C6-C24)alkyl ether carboxylates, preferably (C12-C20) alkyl ether carboxylates;
polyoxyalkylenated (C6-C24)alkyl(amido) ether carboxylic acids and salts thereof, in particular those comprising from 2 to 50 alkylene oxide and in particular ethylene oxide groups;
C6-C24 and especially C12-C20 acylglutamates;
C6-C24 and especially C12-C20 acylglycinates;
In particular in the form of alkali metal or alkaline-earth metal, ammonium or amino alcohol salts.

In certain embodiments, the at least one anionic surfactant of the present invention is chosen from sulfate anionic surfactants which are chosen, alone or as a mixture, from:
alkyl sulfates, especially of C6-C24 or even C12-C20,
alkyl ether sulfates, especially of C6-C24 or even C12-C20, preferably comprising from 2 to 20 ethylene oxide units;
In particular in the form of alkali metal or alkaline-earth metal, ammonium or amino alcohol salts.

In certain embodiments, the anionic surfactant of the present invention is chosen from sulfate anionic surfactants such as sodium lauryl sulfate, sodium laureth sulfate, and mixtures thereof.

In certain embodiments, nonionic surfactants that may be used may be chosen from alcohols, α-diols and (C1-20) alkylphenols, these compounds being polyethoxylated, polypropoxylated or bearing a fatty chain comprising, for example, from 8 to 30 carbon atoms and especially from 16 to 30 carbon atoms, the number of ethylene oxide and/or propylene oxide groups possibly ranging especially from 2 to 50, and the number of glycerol groups possibly ranging especially from 2 to 30.

They may also be made of condensates of ethylene oxide and of propylene oxide with fatty alcohols; polyethoxylated fatty amides preferably having from 2 to 30 ethylene oxide units, polyglycerolated fatty amides containing on average from 1 to 5, and in particular from 1.5 to 4, glycerol groups; ethoxylated fatty acid esters of sorbitan preferably containing from 2 to 40 ethylene oxide units, fatty acid esters of sucrose, fatty acid esters of polyethylene glycol, N—(C6-24 alkyl)glucamine derivatives, amine oxides such as (C10-14alkyl)amine oxides or N—(C10-14 acyl)aminopropylmorpholine oxides.

Preferentially, use is made of ethoxylated fatty acid esters of sorbitan and polyethoxylated fatty alcohols, and mixtures thereof.

Mention may also be made of nonionic surfactants of alkylpolyglycoside type, represented especially by the following general formula: R1O—(R2O)t-(G)v in which:
- $R_1$ represents a linear or branched alkyl or alkenyl radical comprising 6 to 24 carbon atoms and especially 8 to 18 carbon atoms, or an alkylphenyl radical whose linear or branched alkyl radical comprises from 6 to 24 carbon atoms and especially 8 to 18 carbon atoms,
- $R_2$ represents an alkylene radical comprising 2 to 4 carbon atoms,
- G represents a sugar unit comprising 5 to 6 carbon atoms,
- t denotes a value ranging from 0 to 10 and preferably 0 to 4,
- v denotes a value ranging from 1 to 15 and preferably 1 to 4.

Preferably, the alkylpolyglycoside surfactants are compounds having the formula described above in which R1 denotes a saturated or unsaturated, linear or branched alkyl radical comprising from 8 to 18 carbon atoms, t denotes a value ranging from 0 to 3, preferably equal to 0, G denotes glucose, fructose or galactose, preferably glucose; the degree of polymerization, i.e. the value of v, may range from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkylpolyglycoside surfactant is an alkylpolyglucoside surfactant.

Among the commercial products, mention may be made of the products sold by the company Cognis under the names PLANTAREN (600 CS/U, 1200 and 2000) or PLANTACARE (818, 1200 and 2000); the products sold by the company SEPPIC under the names Triton CG110 (or ORAMIX CG 10) and Triton CG312 (or ORAMIX NS 10); the products sold by the company BASF under the name LUTENSOLI GD 70, or the products sold by the company Chem Y under the name AG10 LK. Preferably, use is made of C8/C16-alkyl polyglycosides 1,4, especially as an aqueous 53% solution, such as the product sold by Cognis under the reference PLANTACARE 818 UP.

Preferably, the additional nonionic surfactant(s) are chosen from surfactants of alkylpolyglycoside type such as decyl glucoside, commerically available under the tradename PLANTACARE 2000 UP from the BASF company.

The additional amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, alkyl(C8-C20)sulfobetaines, (C8-C20)alkylamido(C1-C6)alkylbetaines, such as cocamidopropylbetaine, and (C8-C20)alkylamido(C1-C6) alkylsulfobetaines.

Among the optionally quaternized secondary or tertiary aliphatic amine derivatives that may be used, mention may also be made of the products having the following respective structures (A2) and (A3):

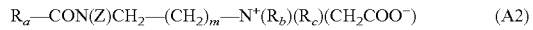

$$R_a\text{—CON(Z)CH}_2\text{—(CH}_2)_m\text{—N}^+(R_b)(R_c)(CH_2COO^-) \quad (A2)$$

in which:
- $R_a$ represents a $C_{10}$-$C_{30}$ alkyl or alkenyl group derived from an acid $R_a$—COOH preferably present in hydrolysed coconut oil, or a heptyl, nonyl or undecyl group;
- $R_b$ represents a β-hydroxyethyl group;
- $R_c$ represents a carboxymethyl group;
- m is equal to 0, 1 or 2;
- Z represents a hydrogen atom or a hydroxyethyl or carboxymethyl group;

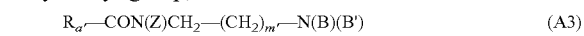

$$R_{a'}\text{—CON(Z)CH}_2\text{—(CH}_2)_{m'}\text{—N(B)(B')} \quad (A3)$$

in which:
- B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom,
- B' represents —(CH$_2$)$_z$—Y', with z=1 or 2, and Y' representing —COOH, —COOZ', CH$_2$—CHOH—SO$_3$H or —CH$_2$—CHOH—SO$_3$Z',
- m' is equal to 0, 1 or 2,
- Z represents a hydrogen atom or a hydroxyethyl or carboxymethyl group;
- Z' represents an ion resulting from an alkali metal or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane,
- $R_{a'}$ represents a $C_{10}$-$C_{30}$ alkyl or alkenyl group of an acid $R_a$COOH preferably present in hydrolysed linseed oil or coconut oil, an alkyl group, in particular a $C_{17}$ alkyl group, and its iso form, or an unsaturated $C_{17}$ group.

The compounds corresponding to formula (A3) are preferred. These compounds are also classified, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, cocoamphodipropionic acid.

Examples that may be mentioned include the cocoamphodiacetate sold by the company Rhodia under the trade name MIRANOL C2M Concentrate or under the trade name MIRANOL ULTRA C 32 and the product sold by the company Chimex under the trade name CHIMEXANE HA.

Use may also be made of compounds of formula (A4):

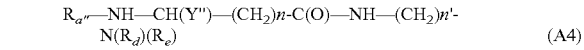

$$R_{a''}\text{—NH—CH(Y'')—(CH}_2)n\text{-C(O)—NH—(CH}_2)n'\text{-N(R}_d)(R_e) \quad (A4)$$

in which:
- $R_{a''}$ represents a $C_{10}$-$C_{30}$ alkyl or alkenyl group of an acid $R_e$—C(O)OH, which is preferably present in hydrolysed linseed oil or coconut oil;
- Y'' represents the group —C(O)OH, —C(O)OZ'', —CH$_2$—CH(OH)—SO$_3$H or the group —CH$_2$—CH(OH)—SO$_3$—Z'', with Z'' representing a cationic counterion resulting from an alkali metal or alkaline-earth metal, such as sodium, an ammonium ion or an ion resulting from an organic amine;
- $R_d$ and $R_e$ represent, independently of each other, a C1-C4 alkyl or hydroxyalkyl radical; and
- n and n' denote, independently of each other, an integer ranging from 1 to 3.

Mention may in particular be made of the compound known under the name sodium diethylaminopropyl cocoaspartamide and sold by the company Chimex under the name CHIMEXANE HB.

Preferably, the amphoteric surfactants are chosen from (C8-C20)alkyl betaines, (C8-C20)alkylamido(C1-C6)alkyl betaines and (C8-C20)alkylamphodiacetates, and also the sodium salt of diethylaminopropyl laurylaminosuccinamate, and mixtures thereof.

The one or more additional surfactants of the present invention may be employed in an amount of from about 0.01% to about 14% by weight, such as from about 0.1% to about 11% by weight, and further such as from about 1% to about 8% by weight, based on the total weight of the hair care composition of the present invention, including increments and ranges therein there between.

The total amount of the additional surfactants in the present invention may be employed in an amount from about 0.01, 0.05, 0.1, 0.5, 1, 2, 3, 4, 5, 6, 7, 8, 9, 10, 11, 12, 13, to about 14 percent weight, based on the total weight of the hair care composition of the present invention, including increments and ranges therein there between.

The compositions according to the invention may additionally comprise cosmetic adjuvants chosen from fragrances, pigments, chelating agents, softeners, antioxidants, opacifiers, stabilizers, moisturizing agents, vitamins, bactericides, preservatives, polymers, thickening agents, or any other ingredient commonly used in cosmetics for this type of application.

Of course, a person skilled in the art will take care to choose this or these optional additional compounds so that the advantageous properties intrinsically attached to the composition in accordance with the invention are not, or not substantially, detrimentally affected by the envisaged addition or additions.

The amounts of these various constituents which can be present in the composition according to the invention are those conventionally used in the art.

The following examples serve to illustrate the invention without however exhibiting a limiting character. In these examples the amounts of the composition ingredients are given as weight percentages relative to the total weight of the composition.

Examples

TABLE 1

Formulation Examples

| Ingredients | Ex. 1 | Ex. 2 | Ex. 3 | Inventive Ex. 4 | Inventive Ex. 5 |
|---|---|---|---|---|---|
| disodium cocoyl glutamate (and) sodium cocoyl glutamate | 15 | 30 | 40 | 30 | 30 |
| hydroxypropyl guar hydroxypropyltrimonium chloride | 0.5 | 0.3 | — | 0.3 | 0.7 |
| glyceryl caprylate | — | — | 8.2 | 5 | 3 |
| Polysaccharides (xanthan gum, pullulan, etc) | 1.1 | — | — | 0.2 | 0.8 |
| Water | Q.S. | Q.S | Q.S | Q.S | Q.S |
| Additional surfactants | 11 | — | — | 20 | — |
| pH adjuster (e.g. Zinc PCA, Citric Acid, etc.) | 0.25 | 0.25 | 0.25 | 1.75 | 0.45 |
| Preservatives (e.g., Sodium Benzoate, Salicylic Acid, etc.) | 0.7 | 0.7 | 0.7 | 0.7 | 0.7 |
| Fatty compounds (e.g. seed oil) | — | — | 10 | — | — |

The viscosity of several conventional formulas were measured and compared to the viscosities of inventive formulas. The viscosities were measured using the Mettler RM 180 Rheomat, viscometer spindle #3, at 25° C.

The present invention is capable of rapidly generating foam on hair that is abundant, dense, translucent, and which rinses out easily.

The present invention used as a shampoo gives on hair a natural and clean feel after removal.

TABLE 2

Formulation and Foaming Evaluation

| Ingredients | Ex. 6 | Ex. 7 Benchmark |
|---|---|---|
| Citric Acid | 0.25 | |
| Decyl Glucoside | | 20 |
| Cocamidopropyl Betaine | | 20 |
| Hydroxypropyl Guar Hydroxypropyltrimonium Chloride | 0.7 | |
| Salcylic Acid | | 0.2 |
| Sclerotium Gum | 0.8 | |
| Salicylic Acid | 0.2 | |
| Sodium Benzoate | 0.5 | 0.5 |
| Glycerin | | 1 |
| Lycium Barbarum Fruit Extract | | 1 |
| Glyceryl Caprylate | 3 | |
| *Yucca Glauca* Root Extract | | 1 |
| Fragrance | | 0.8 |
| Disodium Cocoyl Glutamate (and) Sodium Cocoyl Glutamate | 30 | |
| Zinc PCA | 0.2 | |
| Water | Q.S | Q.S |

TABLE 3

Foaming Evaluation

| | Ex. 6 | Ex. 7 Benchmark |
|---|---|---|
| Flash Foam | 3 | 3 |
| Foam abundance | 3 | 2 |
| Foam stability | 3 | 2 |
| wet detangling | 3 | 2 |
| smoothness wet | 4 | 2 |
| Visual | Translucent | Transparent |
| comments | More slip and conditioned | Sticky, tacky feel |

Rating:
1—Low, 2.5—Average, 5—High

Compared to the benchmark composition in Table 2, Example 7, as shown in the Table 3 and the inventive composition showed improvement in the foam abundance, foam stability, wet detangling and smoothness wet. Additionally, the inventive composition provided more slip and conditioning to hair as compared to the sticky, tacky feel of the benchmark composition on the hair.

The composition according to the invention especially finds a particularly advantageous application in the hair sector, especially for caring for, cleansing and/or conditioning the hair or the scalp. The hair compositions are preferably shampoos, hair conditioners, styling or care gels, care lotions or creams, conditioners, masks, sera, lotions or shampoos for combating hair loss, antiparasitic shampoos, antidandruff lotions or shampoos, or shampoos for treating seborrhoea. Preferably, the composition according to the invention is a shampoo.

The composition according to the invention may be contained in a tube, in a bottle optionally equipped with a pump, or alternatively in an aerosol. In the case of an aerosol, the composition may then contain one or more standard propellants.

Advantageously, the composition according to the invention is in the form of a hair composition for cleansing the hair; preferentially, the composition according to the invention is a shampoo.

The composition may or may not be rinsed out after having been applied to the keratin materials (hair and/or scalp). It is thus optionally possible to perform rinsing, for example with water, after an optional leave-in time. Preferably, it is rinsed out, after an optional leave-in time.

A subject of the invention is also a treatment process or method, especially for caring for, cleansing and/or conditioning keratin materials, especially the hair and/or the scalp, comprising the application to the said materials of a composition according to the invention, optionally followed by rinsing, after an optional leave-in time.

It is in particular a hair treatment process or method, for caring for, cosmetically treating and/or cleansing the hair and/or the scalp.

It is optionally possible to perform rinsing, for example with water, after an optional leave-in time.

The foregoing description illustrates and describes the disclosure. Additionally, the disclosure shows and describes only the preferred embodiments but, as mentioned above, it is to be understood that it is capable to be used in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

The invention claimed is:

1. A shampoo composition comprising, in a cosmetically acceptable solvent:
    a. one or more carboxylate anionic surfactants;
    b. one or more cationic guar compounds, wherein the total amount of the one or more cationic guar compounds is from about 0.3 wt. % to about 1 wt. %, based on the total weight of the shampoo composition;
    c. one or more polysaccharide gums chosen from sclerotium gum, xanthan gum, pullulan, or mixtures thereof, wherein the total amount of the one or more polysaccharide gums is from about 0.1 wt. % to about 5 wt. %, based on the total weight of the shampoo composition; and
    d. one or more glyceryl esters, present in a total amount of at least 2 wt. % based on the total weight of the shampoo composition.

2. The shampoo composition of claim 1, wherein the one or more carboxylate anionic surfactants are selected from acylglycinates, acylsarcosinates, palm itoylsarcosinates, stearoylsarcosinates, lauroylsarcosinates, cocoylacyllactylates, acyllactylates, behenoyllactylates, lauroyllactylates, (iso)stearoyllactylates, acylglutamates, or mixtures thereof.

3. The shampoo composition of claim 1, wherein the one or more carboxylate anionic surfactants are selected from stearoylglutamates, lauroylglutamates, cocoylglutamates, sodium cocoylglutamates, disodium cocoylglutamates, lauryl ether carboxylates, their salts, or mixtures thereof.

4. The shampoo composition of claim 1, wherein the one or more carboxylate anionic surfactants comprises disodium cocoyl glutamate and sodium cocoyl glutamate.

5. The shampoo composition of claim 1, wherein the total amount of the one or more carboxylate anionic surfactants is from about 2wt. % to about 13 wt. %, based on the total weight of the shampoo composition.

6. The shampoo composition of claim 1, wherein the total amount of the one or more carboxylate anionic surfactants is from about 4wt. % to about 12 wt. %, based on the total weight of the shampoo composition.

7. The shampoo composition of claim 1, wherein the one or more cationic guar compounds are selected from hydroxypropyl guar hydroxypropyltrimonium chloride, guar hydroxypropyltrimonium chloride, or mixtures thereof.

8. The shampoo composition of claim 1, wherein the total amount of the one or more polysaccharide gums is from about 0.2wt. % to about 3 wt. %, based on the total weight of the shampoo composition.

9. The shampoo composition of claim 1, wherein the one or more glyceryl esters are_selected from glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or mixtures thereof.

10. The shampoo composition of claim 1, wherein the one or more glyceryl esters are selected from glyceryl caprylate, glyceryl caprylate/caprate, or mixtures thereof.

11. The shampoo composition of claim 1, wherein the total amount of the one or more glyceryl esters is from about 2wt. % to about 6 wt. %, based on the total weight of the shampoo composition.

12. The shampoo composition of claim 1, wherein the total amount of the one or more glyceryl esters is from about 2wt. % to about 5 wt. %, based on the total weight of the shampoo composition.

13. The shampoo composition of claim 1, wherein the cosmetically acceptable solvent is selected from the water, organic solvents or mixtures thereof.

14. The shampoo composition of claim 1, wherein the shampoo composition further comprises one or more secondary surfactants comprising non-carboxylate anionic surfactants, sulfate anionic sulfates, sulfonate anionic surfactant, nonionic surfactants, amphoteric surfactants, or mixtures thereof.

15. The shampoo composition of claim 14, wherein the one or more secondary surfactants are selected from decyl glucoside, lauryl glucoside, coco-glucoside, cocoyl methyl glucamide, disodium laureth sulfosuccinate, sodium lauryl sulfoacetate, or mixtures thereof.

16. The shampoo composition of claim 14, wherein the total amount of the one or more secondary surfactants is from about 0.1wt. % to about 10 wt. %, based on the total weight of the shampoo composition.

17. The shampoo composition of claim 1, wherein the composition is substantially free of sulfate-based anionic surfactants.

18. A method of cleansing hair, the method comprising applying onto hair a shampoo composition comprising, in a cosmetically acceptable solvent:
    a. one or more carboxylate anionic surfactants;
    b. one or more cationic guar compounds, wherein the total amount of the one or more cationic guar compounds is from about 0.3 wt. % to about 1 wt. %, based on the total weight of the shampoo composition;

c. one or more polysaccharide gums chosen from sclerotium gum, xanthan gum, pullulan or mixtures thereof, wherein the total amount of the one or more polysaccharide gums is from about 0.1 wt. % to about 5 wt. %, based on the total weight of the shampoo composition; and d. one or more glyceryl esters, present in a total amount of at least 2 wt. % based on the total weight of the shampoo composition.

19. The method of claim 18, wherein the method provides improved manageability to hair.

* * * * *